United States Patent
Hsia (12)

(10) Patent No.: US 6,294,166 B1
(45) Date of Patent: *Sep. 25, 2001

(54) **NUTRITION SUPPLEMENT CONTAINING *LACTOBACILLUS ACIDOPHILUS*, YEAST AND SOY PROTEIN**

(75) Inventor: Houn Simon Hsia, Foothill Ranch, CA (US)

(73) Assignee: Viva Life Science, Inc., Costa Mesa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/233,638

(22) Filed: Jan. 19, 1999

Related U.S. Application Data

(62) Division of application No. 08/828,143, filed on Mar. 24, 1997.

(51) Int. Cl.$^7$ ..................................................... A01N 63/00
(52) U.S. Cl. ................................... 424/93.45; 424/93.51; 435/252.1; 426/61; 426/62
(58) Field of Search .............................. 424/93.45, 93.51; 435/252.1; 426/61, 62

(56) References Cited

U.S. PATENT DOCUMENTS 4,107,334 * 8/1978 Jolly .
4,897,350 * 1/1990 El-Megeed .
5,108,766 * 4/1992 Gelinas .

FOREIGN PATENT DOCUMENTS

430736 * 11/1990 (EP) .

OTHER PUBLICATIONS

Friend et al., J. Applied Nutrition, 36, vol. 2, pp. 125– (1984).*
Kilara et al., J. Dairy Sci., 61:2031– (1976).*
Shauss et al., J. ADvancement Med., 3:163– (1990).*

* cited by examiner

Primary Examiner—Irene Marx
(74) Attorney, Agent, or Firm—Lyon & Lyon LLP

(57) ABSTRACT

A composition for use as a dietary supplement for promoting gastrointestinal health including effective amounts of a dried bacteria, a dried, non-viable yeast and protein. The dried bacteria may be *Lactobacillus acidophilus*, and may comprise from about 0.1% to about 10% of the total mass of the composition. The yeast may be Brewer's or Baker's yeast, and may comprise from about 2.5% to about 20% of the total mass. The protein may be whey or soy protein concentrates, and may comprise from about 25% to about 98% of the total mass.

5 Claims, No Drawings

NUTRITION SUPPLEMENT CONTAINING *LACTOBACILLUS ACIDOPHILUS*, YEAST AND SOY PROTEIN

This is a divisional of co-pending application Ser. No. 08/828,143 filed Mar. 24, 1997.

BACKGROUND OF THE INVENTION

1. Field of the Invention

The present invention relates to substantially dry, viable bacterial compositions, nutritional supplements containing such compositions, and methods of stabilizing dried viable bacteria.

2. Background

Living bacteria may provide a variety-of nutritional benefits in humans and animals. In particular, bacteria of the genus Lactobacilli are one of the major groups of intestinal and fecal organisms found in humans and animals that are understood to confer certain health benefits to humans and animals. The significant health and nutritional benefits of Lactobacilli, and in particular the strain *Lactobacillus acidophilus*, are well known. [See, e.g., Speck, M. L and Katz, "R. L., "ACDPI Status Paper: Nutritive and Health Values of Cultured Dairy Foods," *Cult. Dairy Prod. J.*, 15(10):4 (1980)]. Lactobacilli found in the human intestinal tract include *Lactobacillus acidophilus*, *Lactobacillus plantatum*, and *Lactobacillus cellobiosus*.

The nutritional benefits of Lactobacilli are manyfold. This genus of bacteria are known to improve the nutritional value of foods by increasing the quantity as well as the availability, digestibility, and assimilability of nutrients. This is accomplished by the fermentation by Lactobacilli of foods, such as proteins, fats, or carbohydrates, that results in the predigestion such foods—in other words, predigestion by Lactobacilli renders the proteins, fats, and carbohydrates in a form that is more readily absorbed and digested in mammals. [Friend, B., Shahani, K., *J. Applied Nutrition*, 36:2 (1984)]. As a result, the nutrients demonstrate an effective increase in their ability to be utilized by the body.

One such compound that Lactobacilli are known to predigest is lactose. Many humans are lactose intolerant—i.e., unable to metabolize lactose (milk sugar)—due to the lack of the β-galactosidase (also known as lactase) enzyme that metabolizes milk sugars. Persons lacking this enzyme may suffer from severe gastrointestinal problems if lactose-containing products are consumed. This nutritional problem may be overcome by *Lactobacillus acidophilus* fermentation since this bacterial species produces β-galactosidase which metabolizes a significant portion of the lactose from the ingested dairy product, thereby preventing gastric complications resulting from its ingestion. [Kilara, A., Shahani, K., *J. Dairy Sci.*, 61:2031 (1976)].

Lactobacilli are also understood to be involved in the synthesis of vitamins. Specifically, depending on the conditions of the bacterial culture, the fermentation of Lactobacilli have been reported to synthesize folic acid, niacin, vitamin $B_{12}$, and vitamin $B_6$. [Friend and Shahani, cited above]. Lactobacilli are also understood to destroy certain anti-nutritional compounds. Certain protein sources, such as raw soybeans, possess anti-nutritional factors such as trypsin-inhibitor, phytate or flatulena. Fermentation of soy by Lactobacilli is understood to reduce or eliminate these factors. [Friend and Shahani, cited above].

Dietary supplementation with *Lactobacillus acidophilus* has been demonstrated as a viable treatment for certain conditions of the intestinal tract including antibiotic-induced imbalances in gastrointestinal microflora, hypercholesterolemia, *E. coli* infection, chronic granulomatous disease, and lactose indigestion. [See, e.q., Shauss, "Method of Action, Clinical Application, and Toxicity Data," *J. Advancement Med.*, 3:163 (1990)]. In addition, Lactobacilli synthesize several antimicrobial substances including lactic acid, acetic acid, benzoic acid, and hydrogen peroxide. [Friend and Shahani, cited above]. By aiding in the predigestion of certain foods, dietary supplementation with Lactobacilli cultures may aid in preventing the over-proliferation of cells. More specifically, diets high in animal fat, protein or fried foods appear to increase the risks of certain kinds of cancers, such as colon and breast cancers. By aiding in the predigestion of fats and proteins, Lactobacilli may be implicated in the inhibition the chemical procarcinogens present in the gastrointestinal tract that result from the digestion of these kinds of foods. [Friend and Shahani, cited above].

Lactobacilli plays important roles in food preservation, since its use is known to assure preservation of highly perishable foods, especially where refrigeration is lacking. The food preservation activity of the compositions of the present invention results from the inclusion of live, stable bacteria that can flourish in the foodstuffs and thereby prevent the overgrowth of other bacteria that may adversely affect the food.

3. Prior Art

Nutritional supplementation of the human diet by orally administered cultured bacterial cultures, including *Lactobacillus acidophilus* preparations, is known. The main problem associated with the use of bacterial cultures in dietary supplementation is the finite shelf-life of live bacteria, i.e., the bacteria will expire after a certain period of time when in dried form and in non-refrigerated storage. Although methods to increase the shelf-life of bacteria used to supplement the diet of humans and animals are known, none has succeeded in maintaining bacterial counts at levels substantially approximating their initial levels after about 180 days, and none are known to actually increase bacterial counts over that time. Moreover, inorganic compounds, such as silicon dioxide polymeric materials, have been proposed to stabilize dried bacterial cultures, [See, e.g., De Silva et al., "Lactic Acid Bacteria on Anhydrous Silica Gel for Three Years," *J. of Food Protection*, 46:699–701 (1983)]. However, such methods are inadequate to sufficiently stabilize bacteria over a period of more than about 180 days. In other words, the efficacy of such nutritional supplements is reduced due to the inherent instability of live *Lactobacillus acidophilus* cultures. Over time, such cultures die and are thus less effective.

For example, U.S. Pat. No. 5,531,988 describes a nutritional composition comprising *Lactobacillus acidophilus* and concentrated immunologically active immunoglobins capable of binding and inactivating antigens that are detrimental to gastrointestinal health. This patent, however, provides no evidence of enhanced viability of the bacteria cultures beyond a period of a few days. In addition, U.S. Pat. No. 5,501,857 describes an oral nutritional supplement for livestock which includes "incompatible" live microbial cultures, such as *Lactobacillus acidophilus*, in combination with, but necessarily physically separated from, a vitamin and mineral composition. As described in this patent, the incompatible ingredients would deleteriously react if combined with one another. Although this patent describes an enhanced shelf-life of the bacteria resulting from the separation of the vitamin and mineral ingredients from the

*Lactobacillus acidophilus* culture, the viability of the bacteria shows a significant decrease over a period of a few months.

Other solid compositions comprising *Lactobacillus acidophilus* have been taught. Various compositions comprising combinations of bacteria with selected carriers are said to aid in increasing the shelf-life of dried bacteria. See, e.g., U.S. Pat. Nos. 3,677,898, 3,898,132, 4,229,544, 4,205,132, 4,518,696, 4,115,199, 3,616,236, and 1,957,555, each of which describe methods to treat dried bacterial compositions in order to increase the shelf-life. Each of the methods disclosed in these patents, however, results in a substantial decrease in bacterial counts over a period of about 180 days or greater. U.S. Pat. No. 4,956,295 is exemplary of efforts to increase the stability of dried bacterial cultures and provides perhaps the best example of the current advances in this field. This patent discloses dried bacterial compositions that combine silicon dioxide particle carrier with mixtures of inorganic salts to increase the shelf-life of the bacteria. However, as is evident from this patent, the shelf-life of *Lactobacillus acidophilus* bacteria exhibited nearly a 100 fold decrease in bacterial counts over a 180 day period. In addition, other bacterial cultures demonstrated a significant decrease in bacterial counts in spite of the disclosed method.

Hence, there remains a need in the art for compositions of solid, dry bacterial cultures, including *Lactobacillus acidophilus* cultures, that are stable for long periods of time under ambient conditions and which are suitable for ingestion by humans and animals.

SUMMARY OF THE INVENTION

The present invention overcomes the shortcomings of the prior art by providing new bacterial compositions, specifically dried bacterial compositions admixed with specific nutrients, where the shelf-life of the bacteria is substantially increased. The present invention provides for new bacterial compositions where the actual bacterial counts, when tested over time under ambient conditions, are not substantially reduced (and may increase) resulting in bacteria that are more stable under ambient conditions for years, rather than days or months.

It is therefore an object of the present invention to provide compositions for use in supplementing the mammalian diet comprising dried bacteria, such as *Lactobacillus acidophilus*, that are stable upon storage at room temperature.

It is another object of the present invention to provide compositions comprising living *Lactobacillus acidophilus* cultures that are useful in the preparation of commercially viable food or food supplement products.

It is another object of the present invention to provide compositions comprising living bacteria, such as *Lactobacillus acidophilus*, that are useful for the manufacturing and processing of foods, and dietary food supplementation products.

It is an other object of the present invention to provide composition comprising living bacterial cultures, such as *Lactobacillus acidophilus*, that are useful in food preservation.

It is a further object of the present invention to provide compositions for use as a nutritional supplement comprising living *Lactobacillus acidophilus* cultures to the human diet that is useful in promoting the health and well being of humans having the condition of lactose intolerance.

It is still a further object of the present invention to provide methods for stabilizing dried bacterial cultures.

DETAILED DESCRIPTION OF THE INVENTION

The above-stated objects of the present invention may be accomplished by providing a composition for use as a dietary supplement for promoting gastrointestinal health comprising: (1) an effective amount of a dried bacteria, such as *Lactobacillus acidophilus*, in combination with; (2) an effective amount of a non-living, dried yeast as a source of carbohydrates, vitamins and minerals; and (3) an effective amount of protein. The effective amount is a combination of these components, when mixed in the dry state, that provides for a composition where, under ambient conditions, the lifetime of the bacteria is substantial, having stability on the order of months to years.

Hence, a method for stabilizing a dried bacterial culture, such as *Lactobacillus acidophilus*, comprises admixing an effective amount of yeast containing carbohydrate, vitamins and minerals, and protein with the dried bacteria such that the resultant mixture consists of each of these ingredients in intimate admixture.

The bacterial component of the present invention may be selected from the strain Lactobacilli. *Lactobacillus acidophilus* is the most preferred strain of Lactobacilli. Other Lactobacilli strains that may be employed in the present invention include *Lactobacillus bulgaricus, Lactobacillus casei, Lactobacillus germentum, Lactobacillus helveticus, Lactobacillus bifudus, Lactobacillus lactis, Lactobacillus delbrueckii, Lactobacillus thermophilus, Lactobacillus fermetti, Lactobacillus coryniformis, Lactobacillus curvatus, Lactobacillus buchneri, Lactobacillus fermentum, Lactobacillus viridescens, Lactobacillus amylovorus, Lactobacillus amylophilus, Lactobacillus pentosaceus, Lactobacillus salivaroes, Lactobacillus brevis, Lactobacillus leichmannii, Lactobacillus plantarum, and Lactobacillus cellobiosus*. These Lactobacilli strains are commercially available. Other genus of bacteria, including but not limited to Streptococci strains, Pedicocci strains, Leuconostoc strains, as well as *Propionibacterium freudenreichii shermanii* may also be stabilized by the methods of the present invention and therefore included as the bacterial component of the compositions of the present invention. More specifically, such Streptococci strains include *Streptococcus lactis, Streptococcus cremoris, Streptococcus diacetylactis, Streptococcus thermophilus, Streptococcus faecium*, and *Streptococcus faecalis*. Pedicocci strains that may be used in the compositions and method of the present invention include *Pediococcus cerevisia, Pediococcus acidilactici*, and *Pediococcus pentosaceus*. Leuconostoc strains that may be used in the compositions and method of the present invention include *Leuconostoc cremoris, Leuconostoc dextranicum*, and *Leuconostoc mesenteriodes*.

The amount of the bacteria in the present invention ranges from about 0.1% to about 10.0%, preferably from about 0.25% to about 5%, and most preferably from about 0.35% to about 0.75% of the total mass of the mixture composition.

The yeast component of the compositions of the present invention may be selected from the group consisting of non-living, dry Brewer's or Baker's yeast. Both of these yeast are sources of carbohydrates, vitamins and minerals upon which the bacteria may derive nourishment, even in their dried state. By providing a source of nourishment for the yeast, the yeast component prevents bacterial counts from decreasing over time and, hence, aids in the stability of the bacterial culture. Such dried yeast are commercially available, and the most preferred yeast form is Brewer's debittered powder [Miller Brewing Co.].

The amount of the yeast employed in the present invention is from about 2.5% to about 20%, and preferably from about 3.0% to about 12.5%, and most preferably from about 4.0% to about 7.5% of the total mass of compositions of the present invention.

The protein source may be chosen from a number of protein sources well known to the art, which include whey protein concentrates, animal protein concentrates, or most preferably, soy protein concentrates. The protein component of the compositions of the present invention includes protein concentrates from a number of commercially available sources. [Protein Technology, CentraSoya, L.A.].

The amount of protein concentrate used in the compositions of the present invention is from about 25% to about 98%, and preferably from about 50% to about 97%, and most preferably from about 75% to about 96% of the total mass of the compositions of the present invention.

When admixed, the dried bacteria, yeast, and protein components of the compositions of the present invention are in a solid, granular form. This form aids in the manufacturing process in that it tends not to clump or stick to the machinery in which it is admixed. The granular solid is freely divided, free-flowing, dry, and may be easily handled. In addition, this form negates the need for excipients to confer desired physical characteristics such as tabletability, compressibility, and the like.

Optionally, excipients such as flavoring agents, flowing agents, anti-caking agents, and other excipients commonly used in pharmaceutical manufacturing processes may be employed in the compositions of the present invention.

To make the compositions of the present invention, the three components are blended. Prior to their blending, the three components are preferably maintained in sealed containers in which they are protected from atmospheric humidity. The components may be combined and blended in standard commercial scale blenders such as a 500 kg Ribbon blender. The components are blended in the blender for a period of time sufficient to assure intimate admixture of all three components, such period of time depending on the amount of material to be admixed and the size of the blender. For example, 150 kg of the composition of the present invention may be admixed for approximately 3 minutes in a 500 kg Ribbon blender.

The compositions of the present invention when in this stable, granular form may be diluted in water and then consumed. A proper dosage of the compositions of the present invention in humans and small animals ranges will depend upon the particular needs of the mammal, and may range from about 0.5 g to about 30.0 g per day, and preferably about 7.5 g per day. In its solid granular form, the compositions of the present invention may be diluted in water and then consumed. A dose of about 7.5 g of the composition of the present invention may be diluted in about 90 mL of water. Alternatively, the compositions of the present invention may be sprinkled onto or admixed with other foods.

The following examples demonstrate preferred embodiments for the present invention and, as such, are illustrative and do not purport to limit the present invention.

EXAMPLE 1

This example illustrates a composition suitable for dietary supplementation to the human diet.

| Ingredient | Amount |
| --- | --- |
| Lactobacillus acidophilus ($1 \times 10^{10}$/g) [Brewster Foods, Inc.] | 1 kg |
| Brewer's debittered powder yeast (Amber 800-40 AG) [Miller Brewing Co.] | 8 kg |
| Soy Protein Isolate (90%) (Profam 982) [CentraSoya, L.A.] | 138.5 kg |
| Chocolate Natural Flavor #9954 [Flavor Producers, Inc] | 2.5 kg |

The ingredients were combined in a 500 kilogram Ribbon blender, and mixed for 3 minutes, then packaged into glass jars which are then sealed such that they are airtight.

EXAMPLE 2

This example describes the stability of the bacterial cultures of Example 1 of the present invention. These data demonstrate that the present invention affords unprecedented vitality to the bacteria, as evidenced by an increase in the total bacterial counts after 18 months.

| Date | Counts Per Gram |
| --- | --- |
| 4/27/95 (date of manufacturing) | $6.35 \times 10^7$ |
| 5/25/95 | $1.10 \times 10^7$ |
| 7/24/95 | $8.30 \times 10^7$ |
| 2/7/96 | $1.00 \times 10^8$ |
| 10/21/96 | $1.50 \times 10^8$ |

Numerous modifications and variations of the present invention are included in the above specification and are expected to be obvious to one of skill in the art. It is also intended that the present invention cover modifications and variations of the compositions and methods using them to accomplish their claimed uses within the scope of the appended claims and their equivalents.

I claim:

1. A method of improving the health of a mammal comprising orally administering to the mammal a nutrition-supplementing amount of a stable, dried bacteria composition comprising, as % total mass of the total dried bacteria composition:

approximately 0.7 percent total mass solid, dried, viable Lactobacillus acidophilus bacteria, approximately 5.3 percent total mass dried, non-living yeast, and approximately 92.3 percent total mass soy protein isolate; wherein the viability of the bacteria in the composition does not decrease for a period of ten months when the composition is stored in an airtight container.

2. The method claim 1 wherein the nutrition-supplementing amount of the stable, dried bacteria composition is in the range of about 0.5 grams per day to about 30.0 grams per day.

3. A method of reducing lactose intolerance in a human comprising orally administering to the human a lactose intolerance decreasing amount of a stable, dried bacteria composition comprising, as % total mass of the total dried bacteria composition:

approximately 0.7 percent total mass solid, dried, viable Lactobacillus acidophilus bacteria, approximately 5.3 percent total mass dried, non-living yeast, and approximately 92.3 percent total mass soy protein isolate; wherein the viability of the bacteria in the composition does not decrease for a period of ten months when the composition is stored in an airtight container.

4. The method of any one of claims 1 or 3 wherein the composition further comprises a flavoring agent.

5. The method claim 3 wherein the lactose intolerance decreasing amount of the stable, dried bacteria composition is in the range of about 0.5 grams per day to about 30.0 grams per day.

* * * * *